United States Patent [19] [11] 4,206,211
Palamidessi et al. [45] Jun. 3, 1980

[54] CEPHALOSPORINS

[75] Inventors: Giorgio Palamidessi; Maurizio Foglio; Franco Zarini; Giovanni Franceschi; Aurora Sanfilippo, all of Milan; Federico Arcamone, Nerviano, all of Italy

[73] Assignee: Farmitalia Carlo Erba S.p.A., Milan, Italy

[21] Appl. No.: 885,126

[22] Filed: Mar. 10, 1978

[30] Foreign Application Priority Data

Mar. 26, 1977 [GB] United Kingdom ............... 12819/77

[51] Int. Cl.$^2$ ............................................ C07D 501/36
[52] U.S. Cl. ....................................... 424/246; 544/21
[58] Field of Search ...................... 544/27, 21; 424/246

[56] References Cited
U.S. PATENT DOCUMENTS

| 3,821,207 | 6/1974 | Chow et al. | 544/27 |
| 3,892,737 | 7/1975 | Ochiai et al. | 544/27 |
| 3,984,403 | 10/1976 | Fujisawa et al. | 544/27 |
| 4,098,888 | 7/1978 | Ochiai et al. | 544/21 |
| 4,128,723 | 12/1978 | Breuer et al. | 544/21 |

OTHER PUBLICATIONS

Cama et al., JACS, 94, 1408 (1972).
Korolkovas et al., Essentials of Medicinal Chemistry, pp. 506–511 (1976).

Primary Examiner—Nicholas S. Rizzo
Attorney, Agent, or Firm—Oblon, Fisher, Spivak, McClelland & Maier

[57] ABSTRACT

7β-acylamino-7α-methoxy-3-pyrazinylthiomethyl-cephalosporins and their intermediates having high resistance toward β-lactamase enzymes, as well as good antibacterial activity and processes for preparation thereof.

6 Claims, No Drawings

CEPHALOSPORINS

The present invention relates to new cephalosporins and to a process for the preparation thereof. More particularly it concerns 7β-acylamino-7α-methoxy-3-pyrazinylthiomethyl-3-cephem-4-carboxylates of general formula:

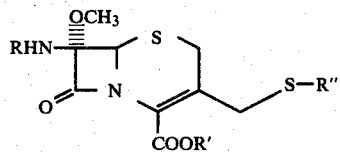

wherein
R is hydrogen or a R'''—CO group in which R''' is selected from the group consisting of cyanomethyl, trifluoromethyl, phenylmethyl, phenoxymethyl, thienylmethyl, tetrazolylmethyl and of a radical having general formula selected from the group consisting of:

in which X is selected from the group consisting of hydrogen, halogen, $C_1$-$C_4$ alkyl, hydroxy, alkoxy, amino; Y is selected from the group consisting of hydroxy, amino, carboxy, sulphonic radical;
R' is selected from the group consisting of hydrogen, pivaloyloxy-methyl, phtalidyl, benzhydryl, trichloroethyl, t-butyl, benzyl, p-nitro-benzyl, p-halophenacyl, trimethylsilyl;
R'' is a pyrazinyl rest of general formula selected from the group consisting of

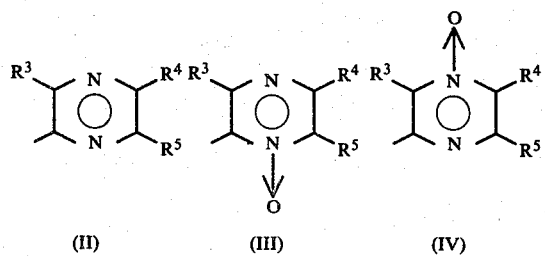

in which $R_3$, $R_4$, $R_5$ are equal to or different from one another and are selected from the group consisting of hydrogen, halogen, $C_1$-$C_4$ alkyl, cyano, thiocyano, carboxy, carboxamido, hydroxy, alkoxy, thiol, alkylthio, amino, alkylamino, phenylamino.

In the Belgian Pat. No. 854845 in the name of the present applicants new 3-pyrazinylthiomethyl cephalosporins (having broad spectrum antibacterial activity) of structure:

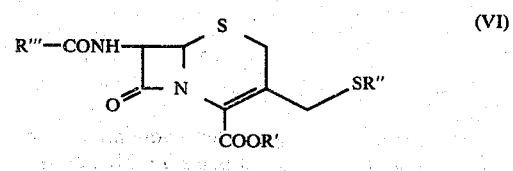

in which R', R'' and R''' have the above meanings have been described and claimed.

This study has been now extended to the corresponding 7α-methoxy analogues, having the general formula (I). They may be prepared by reacting an ester of the 3-pyrazinylthiomethyl-cephalosporins of formula (VI) with an excess of lithium methoxide in tetrahydrofuran-methanol followed by stirring with tert. butyl hypochlorite at low temperature ($-78°\div 80°$ C.) for a few minutes according to the procedure described by (G. A. Koppel and R. E. Koehler, J.A.C.S., 95, 2403, 1973), in accordance with the following scheme:

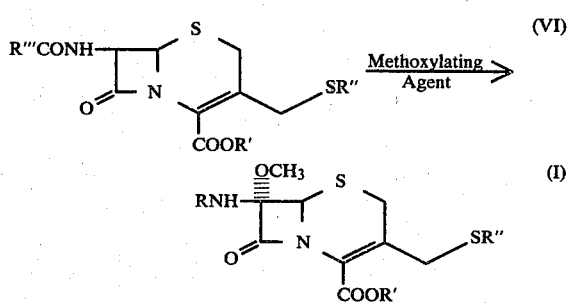

Alternatively, compounds of general formula (I) may be obtained by reacting 7α-methoxy-cephalosporins of formula (V) (described by L. D. CAMA et al., J.A.C.S., 94, 1408, 1972) with the appropriate mercapto pyrazines according to the scheme:

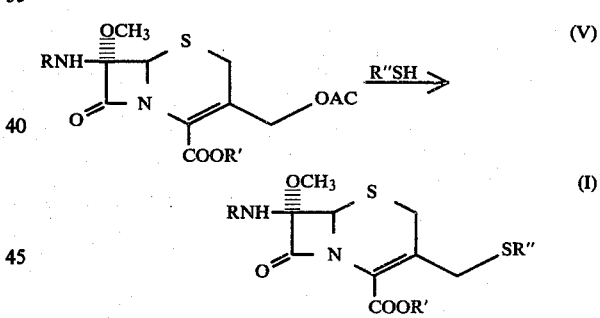

The replacement of the acetoxy group of the compounds of formula (V) may be accomplished following the procedure described in the Belgian Pat. No. 854845. A further alternative process for the preparation of compounds of formula (I) consists in the reaction of the 3-thiolated-7-amino-7α-methoxy-derivative of formula (VII) in which R' and R'' have the above meanings, with a suitable acylating agent such as acid chloride, acid anhydride, acid azide or an activated ester such as para-nitro-phenylester according to the following scheme:

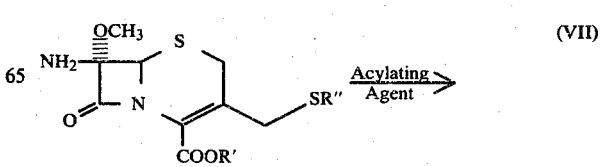

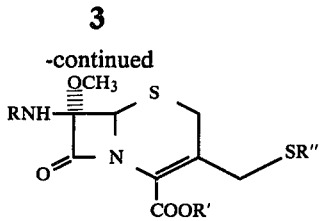

The intermediates (VII), which are new compounds, may be prepared by reacting the corresponding 7-amino-7α-methoxy-cephalosporanate (described by H. Yanagisawa et al., Tetrahedron Letters, 2705, 1975; W. H. W. Lunn and E. V. Mason, ibidem, 1311, 1974) with an appropriate mercaptopyrazine, according to the procedure described in the Belgian Pat. No. 854845. The products of the present invention of formula (I) which are closely related to Cephamycins (R. Nagarajan et al. J.A.C.S. 93, 2308, 1971) show, when R' is hydrogen, a high resistance toward β-lactamase enzymes (such as enzymes from E. cloacae and E. coli), as well a good activity against gram-positive and gram-negative bacteria and are useful in the treatment of infectious diseases. For such purpose, they may be administered either orally or parenterally as free acid or as pharmaceutically acceptable salts. They are also able to inhibit the β-lactamase activity toward sensitive cephalosporins.

In fact, crude enzymes preparations obtained from *Enterobacter cloacae* and *Escherichia coli* are able to hydrolyze 50 μg of sensitive cephalosporins (cephalosporin C, cefazolin) in 1 to 3 minutes, are completely inactive when combined with 25–50 μg of compounds 356/322 and 356/323 as inhibitor, even after 30 minutes of incubation. In order to make the features of the present invention more clear, some non limitative examples of preparation of the new cephalosporins according to the invention are given herebelow.

EXAMPLE 1

7β-(2-Thienyl)-acetamido-7α-methoxy-3-pyrazinylthiomethyl-3-cephem-4-carboxlic acid (356/322)

(a) Diphenylmethyl-7-(2-thienyl)-acetamido-3-pyrazinylthiomethyl-3-cephem-4-carboxylate. This compound was obtained by adding diphenyldiazomethane to a suspension of the free acid prepared according to the procedure described in the Belgian Patent specification No. 854845 in dichloromethane. N.M.R. ($CDCl_3$), δ: 3.48 (dd, C(2)$H_2$), 3.80 (s, $CH_2$—CO), 3.95 and 4.53 (dd, Jgem=14 Hz, exocyclic —$CH_2$—S—), 4.90 (d, C(6)H), 5.76 (dd, C(7)H), 6.6–8.6 (m, benzhydryl, thienyl, phenyl and pyrazinyl protons).

(b) Diphenylmethyl-7β-(2-thienyl)-acetamido-7α-methoxy-3-pyrazinylthiomethyl-3-cephem-4-carboxylate.

To a solution of 700 mg of diphenylmethyl-7-(2-thienyl)-acetamido-3-pyrazinylthiomethyl-3-cephem-4-carboxylate in 15 ml of tetrahydrofuran, cooled to −78° C., was added a precooled solution of 160 mg of MeOLi in 10 ml of methanol. After one minute, 0,14 ml of tert-buthyl hypochlorite was added and the resulting mixture was left at −78° C. for 15 minutes and subsequently quenched with acetic acid and $Na_2S_2O_5$. The solution was diluted with water and extracted with ethyl acetate; after washing with a saturated solution of $NaHCO_3$ and then with water, the orgaic layer was dried over anhydrous $Na_2SO_4$ and evaporated to give 720 mg of a yellow amorphous solid.

N.M.R. ($CDCl_3$) δ: 3.44 (broad s,C(2)$H_2$), 3.51 (s, $CH_3O$), 3.90 (broad s, $CH_2$—CO), 4.10 and 4.66 (dd, Jgem=13 Hz, exocyclic —$CH_2S$—) 5.00 (s, C(6) H), 6.5–8.5 (m, benzhydryl, thienyl, phenyl and pyrazinyl protons). I.R. ($CHCl_3$): 1785, 1730, 1690 cm$^{-1}$.

(c) Hydrolysis of ester to give the title compound.

To a solution of 600 mg of diphenylmethyl-7β-(2-thienyl)-acetamido-7α-methoxy-3-pyrazinylthiomethyl-3-cephem-4-carboxylate in 5 ml of 1,2-dichloroethane, were added at 0° C., 0,600 ml of anisole and 0,900 ml of trifluoroacetic acid. The mixture was left at 0° C. for 30 minutes and then evaporated at room temperature under vacuum. The residue was dissolved in AcOEt and extracted with a solution of $NaHCO_3$. The aqueous layer was washed twice with AcOEt, and extracted, after acidification with HCl2N, with AcOEt. The organic phase was washed many times with water and dried over anhydrous $Na_2SO_4$, giving, after evaporation, 350 mg of an amorphous solid, which was recrystallized from ethyl ether-dichloromethane.

N.M.R. ($CDCl_3$) δ: 3.40 (broad s, (C(2)$H_2$ and $CH_3O$), 3.81 (s, $CH_2CO$), 4.10–4.6 (m, exocyclic —$CH_2$—S), 5.01 (s C(6)H), 6.6–7.6 (m, thienyl protons), 7.8–8.6 (pyrazinyl protons).
I.R. ($CHCl_3$): 1785, 1730, 1700 cm$^{-1}$.

EXAMPLE 2

7β-(2-Thienyl)-acetamido-7α-methoxy-3-(-3-methoxy-pyrazin-2-ylthiomethyl)-3-cephem-4-carboxylic acid (a) Operating as described in Example 1 the following intermediate was obtained: Diphenylmethyl-7-(2-thienyl)-acetamido-3-(3-methoxy-pyrazin-2-ylthiomethyl)-3-cephem-4-carboxylate.

N.M.R. ($CDCl_3$) δ: 3.46 (dd, C(2)$H_2$), 3.80 (s, $CH_2$—CO), 3.93 (s, $CH_3O$), 3.90 and 4.56 (dd, Jgem=14 Hz, exocyclic —$CH_2$—S—), 4.90 (d, C(6)H) 5.83 (dd, C(7)H), 6.7–7.9 (m, benzhydryl, thienyl, phenyl and pyrazinyl protons).

(b) By using the same methoxylation conditions of Example 1, the following compound was obtained.

Diphenylmethyl-7β-(2-thienyl)-acetamido-7α-methoxy-3-(3-methoxy-pyrazin-2-ylthiomethyl)-3-cephem-4-carboxylate.

N.M.R. ($CDCl_3$) δ: 3.48 (broad s, C(2)H and C(7)$OCH_3$), 3.98 (s, aromatic $OCH_3$), 3.80 (broad s, $CH_2$—CO), 4.06 and 4.63 (dd, Jgem=12 Hz, exocyclic $CH_2$—S), 5.00 (s, C(6)H, 6.4–8.1 (m, benzhydryl thienyl, phenyl and pyrazinyl protons).

(c) Hydrolysing the previously described ester the title compound was obtained.

N.M.R. ($CDCl_3$) δ: 3.44 (broad s, C(2)$H_2$ C(7) $OCH_3$), 3.80 (s, $CH_2CO$), 3.97 (s, aromatic $OCH_3$), 5.00 (s, C(6)H), 6.8–8.1 (m, thienyl and pyrazinyl protons).
I.R. ($CHCl_3$): 1780, 1720, 1700 cm$^{-1}$.

EXAMPLE 3

7β-(2-thienyl)-acetamido-7αmethoxy-3-(6-methoxy-pyrazin-2-ylthiomethyl)-3-cephem-4-carboxylic acid (356/323).

A solution of 1.0 g of 7β-(2-thienyl)-acetamido-7α-methoxy-cephalosporanic acid [L. D. Cama et al. J.A.C.S. 94, 1408 (1972)], 0.360 g of 2-mercapto-6-methoxypyrazine, 0,400 g of $NaHCO_3$ in a mixture of 30 ml of water-acetone (2:1) was stirred for 4 hours under reflux.

The acetone was removed under vacuum and the aqueous solution was adjusted to pH 2.0 with 2 N HCl under cooling at 0°-5° C. The resulting crude precipitate was collected by filtration, washed with water and crystallized from aqueous acetone to give yellowish crystalls (0.6 g).

N.M.R. (CDCl$_3$) δ: 3.45 (broad s, C(2)H$_2$ and OCH$_3$), 3.80 (broad s, CH$_2$CO), 3.98 (s, aromatic OCH$_3$), 4.15–4.45 (m, exocyclic CH$_2$S), 5.02 (s, C(6)H), 6.85–8.14 (m, thienyl and pyrazinyl protons).

I.R. (CHCl$_3$): 1780, 1725, 1695 cm$^{-1}$.

What we claim is:

1. Cephalosporins of the formula (I)

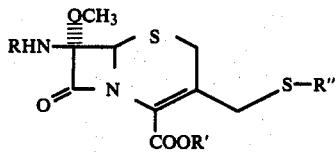

wherein

R is a R'''—CO group in which R''' is selected from the group consisting of cyanomethyl, trifluoromethyl, phenylmethyl, phenoxymethyl thienylmethyl, tetrazolylmethyl and a radical selected from the group consisting of:

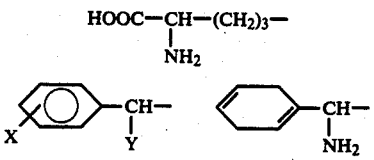

in which X is selected from the group consisting of hydrogen, halogen, C$_1$–C$_4$ alkyl, hydroxy, alkoxy and amino; Y is selected from the group consisting of hydroxy, amino, carboxy and sulphonic radical; R' is selected from the group consisting of hydrogen, pivaloyloxy-methyl, phthalidyl, benzhydryl, trichloroethyl, t-butyl, benzyl, p-nitrobenzyl, p-halophenacyl, trimethylsilyl; and R'' is a pyrazinyl group selected from the group consisting of

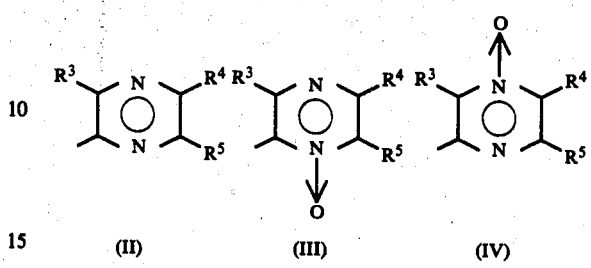

(II) (III) (IV)

in which R$^3$, R$^4$, R$^5$ are the same or different and are selected from the group consisting of hydrogen, halogen, C$_1$–C$_4$ alkyl, cyano, thiocyano, carboxy, carboxamido, hydroxy, alkoxy, thiol, alkylthio, amino, alkylamino and phenylamino.

2. Pharmaceutically acceptable salts of compounds of formula (I) according to claim 1, wherein R' is hydrogen.

3. Pharmaceutical compositions containing one or more compounds of formula (I) according to claim 1, in admixture with a suitable carrier for oral or parenteral administration.

4. The cephalosporin of claim 1 which is 7β-(2-thienylacetamido)-7α-methoxy-3-pyrazinylthiomethyl-3-cephem-4-carboxylic acid.

5. The cephalosporin of claim 1 which is 7β-(2-thienylacetamido)-7α-methoxy-3-(3-methoxypyrazin-2-ylthiomethyl)-3-cephem-4-carboxylic acid.

6. The cephalosporin of claim 1 which is 7β-(2-thienylacetamido)-7α-methoxy-3-(6-methoxypyrazin-2-ylthiomethyl)-3-cephem-4-carboxylic acid.

* * * * *